(12) United States Patent
Shapira et al.

(10) Patent No.: US 11,089,960 B2
(45) Date of Patent: Aug. 17, 2021

(54) CREATION OF ELECTRON DENSITY DATASETS FROM SPECTRAL CT DATASETS

(71) Applicant: KONINKLIJKE PHILIPS N.V., Eindhoven (NL)

(72) Inventors: Nadav Hanan Shapira, Haifa (IL); Amiaz Altman, Tel Aviv (IL); Yoad Yagil, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/632,554

(22) PCT Filed: Jul. 27, 2018

(86) PCT No.: PCT/EP2018/070490
§ 371 (c)(1),
(2) Date: Jan. 21, 2020

(87) PCT Pub. No.: WO2019/016413
PCT Pub. Date: Jan. 24, 2019

(65) Prior Publication Data
US 2020/0155007 A1 May 21, 2020

(30) Foreign Application Priority Data
Jul. 21, 2017 (EP) ..................... 17182477

(51) Int. Cl.
*A61B 5/00* (2006.01)
*A61B 6/03* (2006.01)
*G06T 11/00* (2006.01)

(52) U.S. Cl.
CPC ............ *A61B 5/0073* (2013.01); *A61B 6/032* (2013.01); *G06T 11/005* (2013.01); *G01N 2223/419* (2013.01); *G06T 2207/30004* (2013.01)

(58) Field of Classification Search
None
See application file for complete search history.

(56) References Cited

U.S. PATENT DOCUMENTS

| 6,904,118 B2 | 6/2005 | Wu |
| 2009/0080597 A1* | 3/2009 | Basu ...................... A61B 6/482 378/5 |

(Continued)

FOREIGN PATENT DOCUMENTS

| CN | 103559699 A | 2/2014 |
| CN | 106473761 A | 3/2017 |

(Continued)

OTHER PUBLICATIONS

PCT International Search Report, International application No. PCT/EP2018/070490, dated Oct. 30, 2018.

(Continued)

*Primary Examiner* — Edwin C Gunberg
(74) *Attorney, Agent, or Firm* — Larry Liberchuk

(57) ABSTRACT

A method for converting spectral CT datasets into electron density datasets with applications in the fields of medical image formation or radiation treatment planning. The method comprises a preparation method that fits free parameters of a generalized electron density prediction model based on obtained electron density values such as data on tissue substitutes, and a conversion method using the fitted parameter prediction model and spectrally decomposed CT data as first and second inputs, respectively. The method is particularly useful in dual-energy CT and more specifically in dual layer detector CT systems.

9 Claims, 6 Drawing Sheets

(56) References Cited

U.S. PATENT DOCUMENTS

2009/0262997 A1  10/2009  Zou
2010/0089754 A1   4/2010  Mizuno

FOREIGN PATENT DOCUMENTS

EP       2749219 A1   7/2014
WO    2016147844 A1   9/2016

OTHER PUBLICATIONS

Han D0ng et al., "A Linear, Separable Two-Parameter Model for Dual Energy CT Imaging of Proton Stopping Power Computation", Medical Physics, AIP, Melville, NY, US, vol. 43, No. 1, Jan. 8, 2016 (Jan. 8, 2016), pp. 600-612, XP012203786.
Chia-Ho Hua et al., "Accuracy of Electron Density, Effective Atomic Number, and Iodine Concentration Determination with a Dual Layer Dual Energy Computed Tomography System", Medical Physics, vol. 45, No. 6, Apr. 6, 2018 (Apr. 6, 2018), pp. 2486-2497, XP055516305.
Kuo Men et al., "A Method to Improve Electron Density Measurement of Cone-Beam CT Using Dual Energy Technique", Biomed Research International, vol. 2015, Jan. 1, 2015 (Jan. 1, 2015), pp. 1-8, XP055444761.
Szczykutowicz Timothy P et al., "A Simple Image Based Method for Obtaining Electron Density and Atomic Number in Dual Energy CT", Medical Imaging 2011: Physics of Medical Imaging, SPIE, 1000 20th St. Bellingham WA 98225-6705 USA, vol. 7961, No. 1, Mar. 3, 2011 (Mar. 3, 2011), pp. 1-6, XP060008261.
Griffiths, H. J. et al., "Tissue Substitutes in Radiation Dosimetry and Measurement", Report 44 of the International Commission on Radiation Units and Measurements (ICRU), Radiology, vol. 173,issue 1, pp. 202-202, Oct. 1989.

\* cited by examiner

CREATION OF ELECTRON DENSITY DATASETS FROM SPECTRAL CT DATASETS

FIELD OF THE INVENTION

This invention generally relates to the field of image reconstruction in Computed Tomography (CT) scanning systems and, in particular, relates to the creation of electron density images in Dual Energy Computed Tomography scanning systems.

BACKGROUND OF THE INVENTION

Computed Tomography (CT) scanning systems are diagnostic tools that are ubiquitous in today's modern medical health care infrastructure. CT scanners implement a medical imaging technique based on X-ray absorption characteristics and therefore allow non-invasive investigation of anatomical structures located inside the body, e.g. bones, tissues, organs, etc. Modern industrial technology also sought for non-destructive inspection systems, which led to the development of industrial CT scanning systems. They are commonly used for quality control of materials, e.g. welded metal pieces, such as for instance detecting and characterizing potential risks due to porosity, structural defects, cracks, etc.

From a historic perspective, however, CT scanners have been developed for medical screening of humans. This is reflected by the standard Hounsfield radiodensity units (HU) used in medical CT applications which are defined in terms of linear attenuation coefficients for water and air under standard temperature and pressure conditions. These two forms of matter are naturally found in big parts of the human body tissues. Metallic structures within the body instead, such as hip implants, stents, or screws, show a very different absorption behavior in comparison to biological substances. Indeed, it is known in CT literature that the presence of metals inside the body often induces streaking and cupping artifacts in the reconstructed images, thus drastically reducing their diagnostic usefulness. These artifacts are in part attributed to beam hardening (BH) which occurs whenever the lower energetic spectral components of a polychromatic X-ray beam experience stronger absorption than the higher energetic spectral content, leading to an upward shift of the beam's mean spectral energy. Beam hardening is particularly strong for metallic materials, but also exists to some extent for organic materials, such as bone, and for commonly used contrast agents, such as iodine. BH artifacts, and therefore standard CT radiodensity units (HU), depend on the spectral width of the X-ray beam as well as on the patient's position, size, and inner anatomy. Correcting for the limiting contributions of BH and metal artifacts in standard CT scans does not only improve image accuracy and contrast, but also contributes to more accurate radiotherapy treatments that are simulated or planned based on input data from standard CT scans. Especially relevant in that aspect is the creation of accurate electron density images upon which the calculation of proton stopping powers in proton therapy are founded.

Spectral CT in general, and Dual Energy CT in particular, collect additional spectral information of the tissues irradiated by the polychromatic X-ray beam. Exploiting well-known material and energy dependencies of the attenuation of X-ray photons, spectral CT methods enable a spectral image decomposition which allows to distinguish between intrinsic material attenuation and local density. The spectral CT approach has already found many interesting applications being built upon equivalent material decomposition models, for instance Kidney stone differentiation, tissue differentiation, material decomposition of biological tissues, colonoscopy CT and polyp detection, K edge detection, enhancing signals from low concentration contrast agents, BH correction, metal artifact reduction, etc. Decomposition models carried out in a post-processing step are appreciated for their ease of implementation, processing speed and modest demand on computing resources, as they are often stated in matrix form for solving a linear system of equations. More importantly, spectral CT techniques allow for a reduction in radiation doses and injected contrast agents. There exist four common techniques to acquire dual energy CT images: fast kVp-switching, dual-source CT, dual-layer sensor CT, and sequential CT scanning.

The technological advancement of spectral CT and its related additional spectral information provided is also of benefit to proton radiotherapy treatment as the creation of more accurate electron density images leads to more accurate calculations of proton stopping powers and hence to lower administering of radiation doses and to more targeted irradiation spots leaving surrounding tissue intact.

EP2749219A1 (TSINGHUA UNIVERSITY, NUCTECH COMPANY LIMITED) discloses a multi-energy CT device and an imaging method for obtaining electron density images. The electron density images are created by applying a decomposition model to attenuation coefficients of hybrid reconstructed multi-energy CT images in a post-processing procedure and by predicting the electron densities as a sum of known base material electron densities weighted by the respective decomposition coefficients. A fixed relationship between predicted electron densities and decomposition coefficients is assumed. It is a disadvantage that the electron densities calculated by such a restricted relationship may not be equally accurate over a wide range of tissues having dissimilar constituents, such as soft tissues and bone, and for a selected base material pair.

SUMMARY OF THE INVENTION

It is an object of embodiments of the present invention to provide an accurate method and device for converting CT datasets into electron density datasets.

In order to achieve the objective mentioned above, the present invention provides, in a first aspect, a preparation method for predicting electron densities and a method for converting spectral CT datasets into electron density datasets.

The preparation method comprises the following steps. In a first step, first attenuation coefficients representing attenuation characteristics of at least one material mixture are modeled as a combination of second attenuation coefficients of constituent elements of the at least one material mixture for a first set of at least two different values of physical phenomena contributing to attenuation, for example at least two different X-ray photon energy values. In a second step, base components of a material decomposition model for each of the at least one material mixtures are determined, each base component being a function of the first attenuation coefficients. The determination is performed by solving a system of equations relating said first attenuation coefficients to combinations of known base material attenuation coefficients determined by a second set of at least two different values of physical phenomena contributing to attenuation, for example two different X-ray photon energy values. In a third step, a parametrized function of said two base components is fitted to obtained electron densities of said material mixtures, thus obtaining a function with a set of fitted parameters predicting electron densities of the material mixtures.

In some embodiments of the present invention the first and second set of physical phenomena contributing to attenuation may be the same, e.g. the attenuation of X-rays at two different energy values. In alternative embodiments one or both of the sets of physical phenomena contributing to attenuation may be given by attenuation measurements of protons or neutrons.

The method for converting spectral CT datasets into electron density datasets comprises the following steps. Firstly, at least a set of fitted parameter of a function predicting electron densities of material mixtures is obtained, e.g. retrieved from a storage medium, whereby the set of fitted parameter is obtained by carrying out the steps of the preparation method as set out above. Secondly, a spectral CT dataset comprising a plurality of measurement points is obtained and base components are extracted for each measurement point within the CT dataset. Finally, the function with the set of fitted parameters is applied to the extracted base components, thus obtaining an electron density dataset.

The preparation method for obtaining a function with a set of fitted parameters predicting electron densities of material mixtures may be followed immediately by the application of this function to extracted base components so as to obtain the electron density dataset, but this does not have to be the case. In alternative embodiments, obtaining the electron density dataset may be done based on a function with a set of fitted parameters prediction electron densities of material mixtures, which function was obtained by means of a preparation method carried out earlier. The defining function and the set of fitted parameters may be stored on a suitable computer-readable storage medium for this purpose.

In particular embodiments of the present invention, a method for converting spectral CT datasets into electron density datasets may thus comprise:

Modeling first attenuation coefficients representing attenuation characteristics of at least one material mixture as a combination of second attenuation coefficients of constituent elements of the at least one material mixture for at least two different values of physical phenomena contributing to attenuation;

Determining base components of a material decomposition model for each of the at least one material mixtures, each component being a function of the first attenuation coefficients, the determining being performed by solving a system of equations relating said first attenuation coefficients to combinations of known base material attenuation coefficients at the at least two different values of physical phenomena contributing to attenuation; Fitting a parametrized function of said two base components to obtained electron densities of said material mixtures, thus obtaining a function with a set of fitted parameters predicting electron densities of the material mixtures;

Obtaining a spectral CT dataset comprising a plurality of measurement points, extracting base components for each measurement point within the CT dataset, and applying the function with the set of fitted parameters to the extracted base components, thus obtaining an electron density dataset.

In a method according to embodiments of the present invention, the combination of second attenuation coefficients of constituent elements of the at least one material mixture may be a linear superposition. The second attenuation coefficients of constituent elements of the at least one material mixture may be expressed as weighted mass attenuation coefficients; the weight corresponding to the given mass fraction of a constituent element in the material mixture.

In a method according to embodiments of the present invention, the second attenuation coefficients of constituent elements of the at least one material mixture may be inferred from obtained data on tissue composition and obtained data on mass attenuation coefficients.

In a method according to embodiments of the present invention, the system of equations relating said first attenuation coefficients to combinations of known base material attenuation coefficients at the at least two different values of physical phenomena contributing to attenuation may be a system of linear equations.

In embodiments of the present invention, the fitting a parametrized function of said two base components to obtained electron densities of said material mixtures may involve fitting a polynomial function of said two base components to obtained electron densities of said material mixtures. The polynomial function may be of degree one.

In some embodiments of the present invention, a polynomial model may hence be used as the function predicting electron densities, for instance in particular a linear function may be used. This has a positive impact on evaluation speed which is a critical parameter in real-time CT imaging. Moreover, this allows for faster model optimization, i.e. parameter fitting, and model quality check as well. Indeed, it is possible to rapidly switch between different models for different CT applications or to quickly select a better model or even the best model out of a bag of models.

In some embodiments of the present invention, the parameter fitting strategy relies on decreasing the sum of residual errors under the L1 norm below a given error threshold value. The L1 norm is also known as least absolute deviations, or least absolute errors. It is basically minimizing the sum of the absolute differences between a target value (obtained value) and the predicted values. Choosing the L1 norm as error norm for absolute differences in electron densities between predicted and obtained values has the benefit of reducing the importance attributed to outliers. Furthermore it intentionally diverts additional weight to tissues with high expected electron density, such as bone, for which electron density accuracy is most significant in radiation planning.

In some embodiments of the present invention, the acquired spectral CT datasets may be obtained by dual-energy CT, and more specifically by dual-layer detector CT systems. The latter do not require additional secondary sources nor repeated scans. It is also sufficient to calibrate the sensor to only one X-ray source and the field of view is constant. No special care has to be attributed to image registration and interpolation schemes in such systems, which together with the fast scanning in helical CT scanners, makes it an attractive candidate for real-time monitoring of moving organs, e.g. the heart, or to study the uptake of drugs or contrast agents.

In embodiments of the present invention, the decomposition model may be a two base material decomposition. This is of particular interest to computational efficiency in terms of speed and resources, as these base material decomposition models may be easily implemented in matrix form describing a linear system of equations that needs to be solved. Moreover, base material decomposition models have been successfully implemented in order to increase the image contrast in cases where the contrast agent is of low concentration only or where small difference in the local tissue composition are difficult to spot otherwise. This has numerous positive impacts on early diagnosis and decision making.

In a second aspect, the present invention provides a data-processing device for converting spectral CT datasets into electron density datasets. The data-processing device comprises An input port for receiving at least a set of fitted parameter of a function predicting electron densities of material mixtures; said set of fitted parameter being obtained by carrying out the steps of embodiments of the preparation method of the present invention, An input port for receiving a spectral CT dataset comprising a plurality of measurement points, and a processing device for extracting base components for each measurement point within the CT dataset, and applying the received function with the set of fitted parameters to the extracted base components, thus obtaining an electron density dataset.

The data-processing device may further comprise a storage unit for storing data and for allowing data to be retrieved therefrom. It may comprise means for carrying out the steps of a conversion method in accordance with embodiments of the first aspect of the present invention.

In embodiments of the present invention, the data-processing device may be a computer, a computer cluster, a GPU array, a microprocessor or an FPGA, so arranged as to carry out method embodiments according to the first aspect of the present invention. It is an advantage of embodiments of the present invention that the conversion method may be easily parallelized and distributed over the computing hardware such that electron density datasets and visualizations thereof may be quickly obtained.

In a third aspect, the present invention provides a computer program product that comprises instructions that cause a data processing device according to embodiments of the second aspect of the invention to perform the steps of the conversion method in accordance with embodiments of the first aspect of the present invention.

In embodiments of the present invention, the computer program product may be stored on a data carrier, and the present invention includes a data carrier such as a CD-ROM, a memory key, a diskette, a USB stick, a CD or DVD, an SD card, which stores the computer product in a machine readable form and which executes at least one of the methods of the invention when executed on a data-processing device.

In a fourth aspect, the present invention provides a transmission of data via compact storage media, e.g. USB sticks, CDs, SD cards or DVDs, or over a network, such as e.g. the internet, that causes a data processing device according to the second aspect of the invention to perform the steps of the conversion method in accordance to the first aspect of the present invention. Such transmission makes the conversion method for converting CT datasets into electron density datasets largely available to clinics and institutions and enterprises in the field of medical healthcare which may use the deployed software to obtain more accurate electron density estimates, for instance as inputs to radiation therapy planning systems or software. This in turn leads to more accurate calculations of proton stopping powers, for example, which has many benefits to the patient, for instance a reduction in the administered dose, or an improved focusing of the proton beam leaving surrounding healthy tissue intact.

Particular and preferred aspects of the invention are set out in the accompanying independent and dependent claims. Features from the dependent claims may be combined with features of the independent claims and with features of other dependent claims as appropriate and not merely as explicitly set out in the claims.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, in which:

FIG. 3 and FIG. 4, respectively, show absolute and relative differences for the two dose levels. FIG. 5 and FIG. 6 illustrate relative differences separated into the different dose levels.

DETAILED DESCRIPTION OF ILLUSTRATIVE EMBODIMENTS

Figure 1:
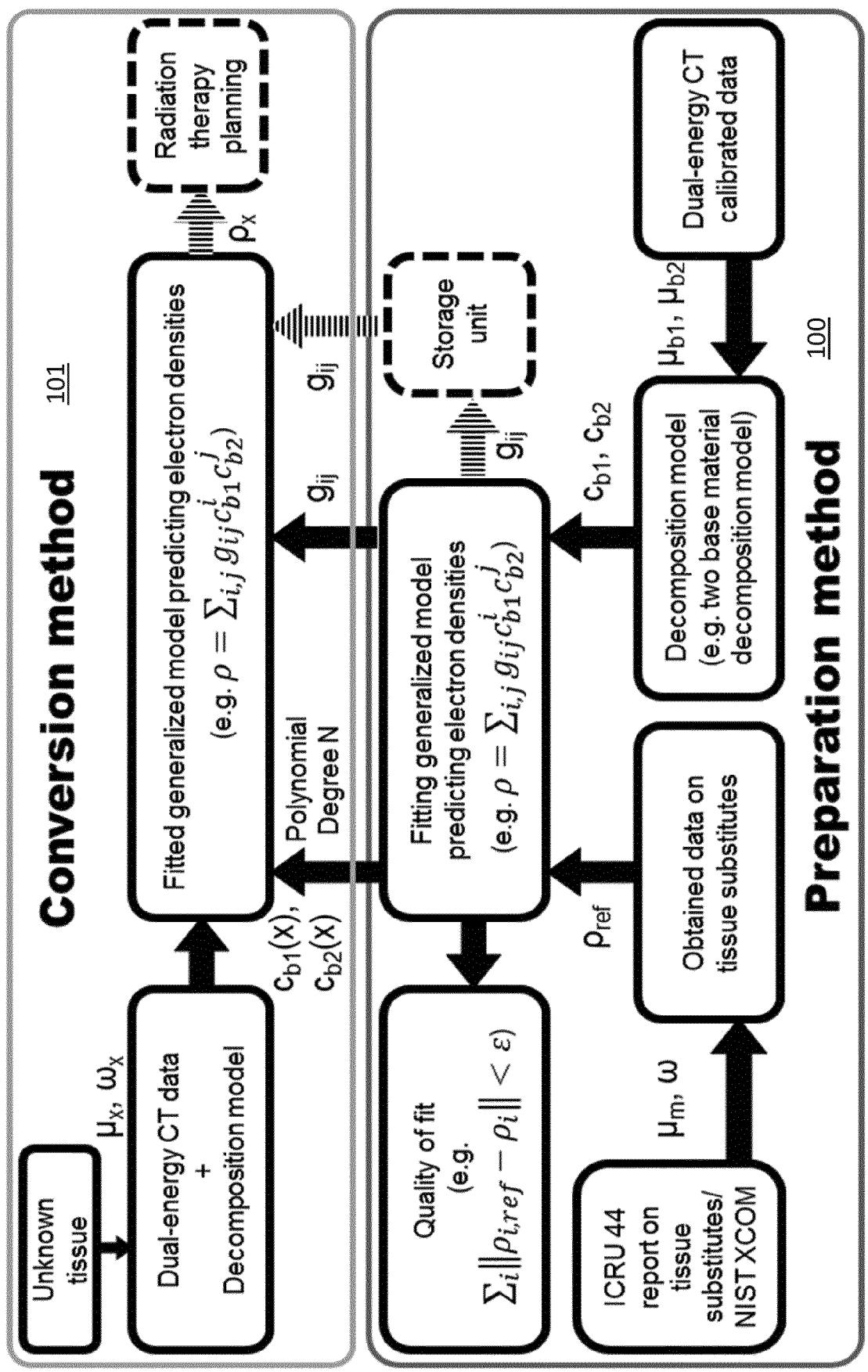
FIG. 1 shows a process flow diagram illustrating the steps of both a preparation and a conversion method according to embodiments of the present invention.

The present invention will be described with respect to particular embodiments and with reference to certain drawings but the invention is not limited thereto but only by the claims.

The terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

The flow chart of FIG. 1 summarizes the main steps of a preparation method 100 and a conversion method 101 according to embodiments of the present invention. The preparation method 100 aims to obtain a parametrized function together with a specific set of parameters that is first input to the subsequent conversion method 101, the conversion method 101 converting CT datasets into electron density datasets. It is an advantage of embodiments of the present invention that the conversion method 101 uses spectral CT datasets, e.g. datasets recorded by a dual-layer detector CT scan, as second inputs, and thereby efficiently exploits the extra spectral energy information content conveyed by such scan. One way to exploit the additional spectral energy dimension is the introduction of a decomposition model. This model decomposes the measured attenuation coefficients that may be obtained by scanner specific calibration curves from the standard CT Hounsfield units into two or more equivalent decomposition coefficients that represent the biological tissue or substance under test as an equivalent mixture of known and characterized base materials. A common model in dual-energy applications is the linear two base material decomposition model mathematically expressed in Eq. 1:

$$\mu_{x,cT}(r,E) = c_1(r)\mu_{b,1}(E) + c_2(r)\mu_{b,2}(E) \quad \text{(Eq. 1)}$$

A special feature of the linear two base material decomposition model is its capability to factor space and energy dependence of the measured attenuation coefficient from a CT data point of unknown material composition into an only space dependent coefficient related to mass density of the known base material ($b_1, b_2$) and an energy dependent, intrinsic attenuation term. It is seen that such decomposition model may be used to overcome the qualitative nature of standard CT Hounsfield units and introduce a more quantitative way of performing CT scans; mass density and local, intrinsic material constituents may be identified successfully by such a model.

Depending on the scanned body region or medical examination, different base materials may be selected, e.g. soft tissue and bone, if the target is to increase image contrast in regions where bone and soft tissues overlap or one may wish to subtract bone out of the image. Another example may be the differentiation of kidney stones, in which case one may choose a material base pair that differentiates well radiolucent, low atomic number mixtures for uric acid from radiopaque, higher atomic number mixtures for calcium oxalate. It is advantageous to use material decomposed CT datasets in embodiments of the invention, as this often allows for a dose reduction during the patient scan. The possibility to apply iterative, forward correction methods in order to reduce metal artifacts, to reduce noise and scattering contributions, and to compensate for BH effects constitutes another important advantage of using material decomposed CT datasets in embodiments of the invention.

It is apparent from Eq. 1 that space dependent decomposition coefficients $c_1$, $c_2$, which may correspond to scanned body regions averaged over the size of a voxel in clinical CT runs, may be derived if such equation is established for at least two differing energy values. These two energy values are often referred to as an energy pair in dual-energy CT. In particular embodiments of the present invention, this energy pair or plurality of energy values may be the mean energy values of a kVp-switched or dual X-ray source, e.g. 45 keV and 80 keV for 80 keV and 140 keV tube voltages. In alternative embodiments this energy pair or plurality of energy values may be obtained from the energy selecting layers of a spectral dual-layer X-ray detector or a photon counting, energy resolving pixel detector array. Typically dual X-ray sources and dual layer X-ray detectors are designed in such a way that they try to increase or maximize separation of the X-ray energy bands; minimal overlap of the spectral X-ray bands may indeed increase the electron density prediction accuracies. If Eq. 1 is established at more than two energy values, or if an additional constraint, e.g. mass conservation, is applied, more than two decomposition coefficients, e.g. three decomposition coefficients, may be derived if Eq. 1 is extended to comprise other base material terms. It is an advantage of embodiments of the invention that the system of linear equations in matrix form of Eq. 1 may be solved for the decomposition coefficients at each data point by efficient established algorithms, e.g. LU decomposition or Cholesky factorization, with no substantial computational time and load added. This is in contrast to iterative nonlinear decomposition techniques, e.g. the nonseparable ρ-Z decomposition method, which require substantial computational effort and are often implemented as a pre-processing step using forward projection-correction. Beside the dependency on space, the decomposition coefficients depend on the unknown tissue or material mixture under study and located at that specific data point the space variable is hinting at. Different tissue compositions and types thus give rise to different value sets of the decomposition coefficients via their specific attenuation coefficients $\mu_{x;CT}$. Therefore it is an advantage of embodiments of the invention that the tissue composition information, e.g. information on a material mixture, encoded in the derived value set of the decomposition coefficients at each data point is exploited with regard to electron density estimations at these data points. In theoretical and experimental treatments it is commonly assumed that linear attenuation coefficients and electron density are directly proportional to each other. This approach is reflected in prior art research and inventions that try to combine the benefits of the two base material decomposition model with the possibility of obtaining electron density estimations from dual-energy CT scans: in agreement with Eq. 1 and under the assumption of a fixed proportionality constant, the estimated electron density p of the two base material decomposition is expressed as indicated in Eq. 2.

$$\rho_{x,CT}(r) = c_1(r)\rho_{b,1} + c_2(r)\rho_{b,2} \qquad (Eq.\ 2)$$

Eq. 2 is an approximation of the electron density. Although it is stated in a convenient form, easy to evaluate, and satisfying in some cases, it might be necessary to further improve on the predicted electron density values, e.g. for precise radiotherapy planning systems that rely on accurate electron density images. The assumption of proportionality between attenuation coefficient and electron density is founded in approximate expressions of the photon scattering cross sections at clinical X-ray energies. However, it is also true that the coefficient of proportionality is not a constant, but depends on the X-ray photon energy as well as on the atomic number Z. Depending on whether the tissue has a uniform effective atomic number or includes contributions from high Z number materials, the electron density estimates derived from Eq. 2 will be more or less accurate. If the base material electron density values or decomposition coefficients are obtained by experimental means, the averaging effect over energies contained in a polychromatic X-ray beam described by a mean energy value and measurement noise contributions eventually leads to other nonlinearities and imprecisions not accounted for in Eq. 2. One suggested way to overcome the impact of high atomic number contributions in particular types of tissues is to switch the base material pair. However, the switching threshold value and the replacement of the first base material pair by a second one are empirical choices and may not meet the expected performance criteria under particular circumstances. It also necessitates the careful characterization of a second base material pair. In embodiments of the invention, accurate electron density estimates are obtained by generalizing the functional relationship of Eq. 2 so as to introduce a more flexible model for electron density predictions. It is an advantage of particular embodiments of the invention that a unique base material pair of a two base material decomposition model can be used to obtain accurate electron density estimations. Furthermore, it is an advantage of embodiments of the invention that a generalized model may partially or wholly compensate for several of the mentioned error contributions, such as X-ray spectral energy range dependence, approximation errors due to the assumption of proportionality between attenuation coefficient and electron density, as well as measurement noise, artifacts, and nonlinearities. In particular embodiments of the invention, the generalized model will be a polynomial model, including a linear model; this is described in Eq. 3 with $g_{ij}$ as the polynomial coefficients. For such particular embodiments, the electron density estimation is easily computed without a substantial computational load or time. Furthermore, and in contrast to approaches according to Eq. 2, it is not necessary to provide prior information on the electron density values of the base material pair which may be difficult to obtain or characterize.

$$\rho_{x,CT}(r) = \Sigma_{ij} g_{ij} c_1^i(r) c_2^j(r) \qquad (Eq.\ 3)$$

In embodiments of the invention the preparation method aims at providing a set of fitted parameters, e.g. the polynomial coefficients $g_{ij}$, that are deployed in the subsequent conversion method as first inputs to a function predicting electron density estimates, e.g. the function of Eq. 3. The conversion method is applied to CT datasets and creates electron density datasets. In embodiments of the invention, the CT dataset may comprise a sequence of voxels to which the decomposition coefficients of a decomposition model are assigned, for instance the coefficients of a two base material decomposition model $c_1$, $c_2$ that reflect the two equivalent mass densities of the two selected base materials inside the voxel volume. For such embodiments, the conversion method will map the decomposition coefficients of each voxel of the CT dataset (second inputs to the electron density prediction function) to electron density estimations for the very same voxel, using for instance Eq. 3. The sequence of thus obtained electron density estimates is comprised in an electron density dataset which may be visualized and interpreted as one or more electron density images.

Having the preparation method output a set of fitted parameters as first inputs to a function predicting electron density estimates, a suitable fitting procedure is needed. In embodiments of the present invention such a fitting procedure may comprise adapting the parameters in a way such that the predicted output of the function lies close to a specified target value. "Close" in this case means within predefined error margins and according to a suitable error measure. In particular embodiments, the target value may be an obtained reference value for the electron density of the respective material mixture, e.g. body tissue, such as adipose or cortical bone, etc. Such reference value for the electron density may be obtained by a characterizing experiment that was conducted earlier on, or it may be retrieved from published reports, e.g. the ICRU 44 report 'Tissue Substitutes in Radiation Dosimetry and Measurement', Report 44 of the International Commission on Radiation Units and Measurements (ICRU), Bethesda, Md. It is an advantage of such particular embodiments to refer to reported electron density values of tissue substitutes as those reported values are generally obtained under high experimental standards eliminating many deleterious error sources that would otherwise lead to higher uncertainties and that would propagate to less accurate electron density prediction results of the fitted function. For such embodiments, a suitable error measure may be the sum of residual errors under the L1 norm of all the retrieved reference values of electron densities of a given tissue substitute as is indicated in Eq. 4 with $\rho_{i,CT}$ being the output value of the generalized model of Eq. 3 for a given tissue substitute 'i' of the report. A way to determine the decomposition coefficients as they enter in Eq. 3 for such a given tissue substitute 'i' of the report is explained at a later stage.

$$\text{Error} = \Sigma_i^{Nr\ tissues\ in\ ICRU\ 44} |\rho_{i,CT} - \rho_{i,report}| \qquad (Eq.\ 4)$$

Figure 2:
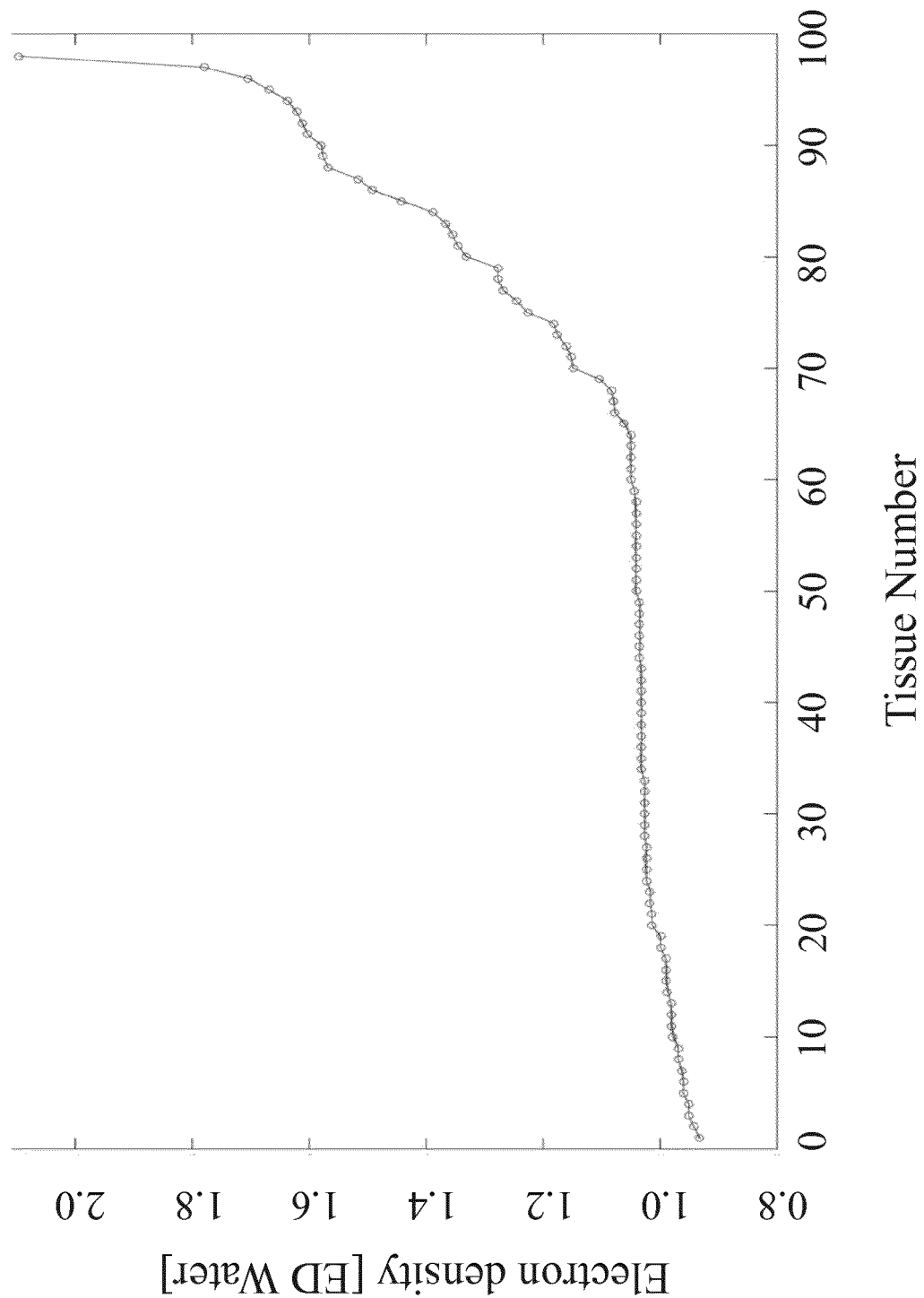
FIG. 2 displays reference values and fitting results for a linear electron density predicting function for a large set of ICRU 44 tissue substitutes.
Figure 3:
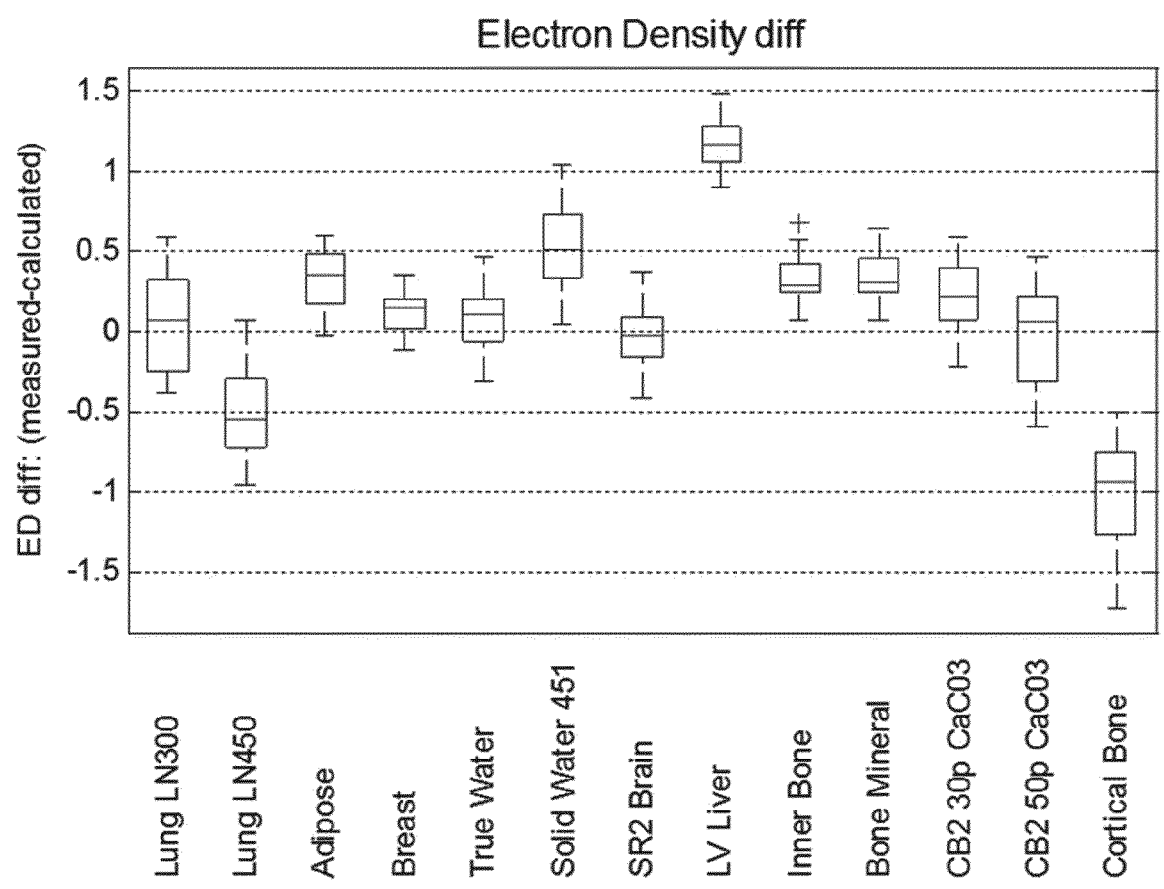
FIG. 3 to FIG. 6 display absolute and relative differences between experimentally obtained and calculated electron densities at two different dose levels (250 mAs and 500 mAs) for a tissue characterization phantom.
Figure 4:
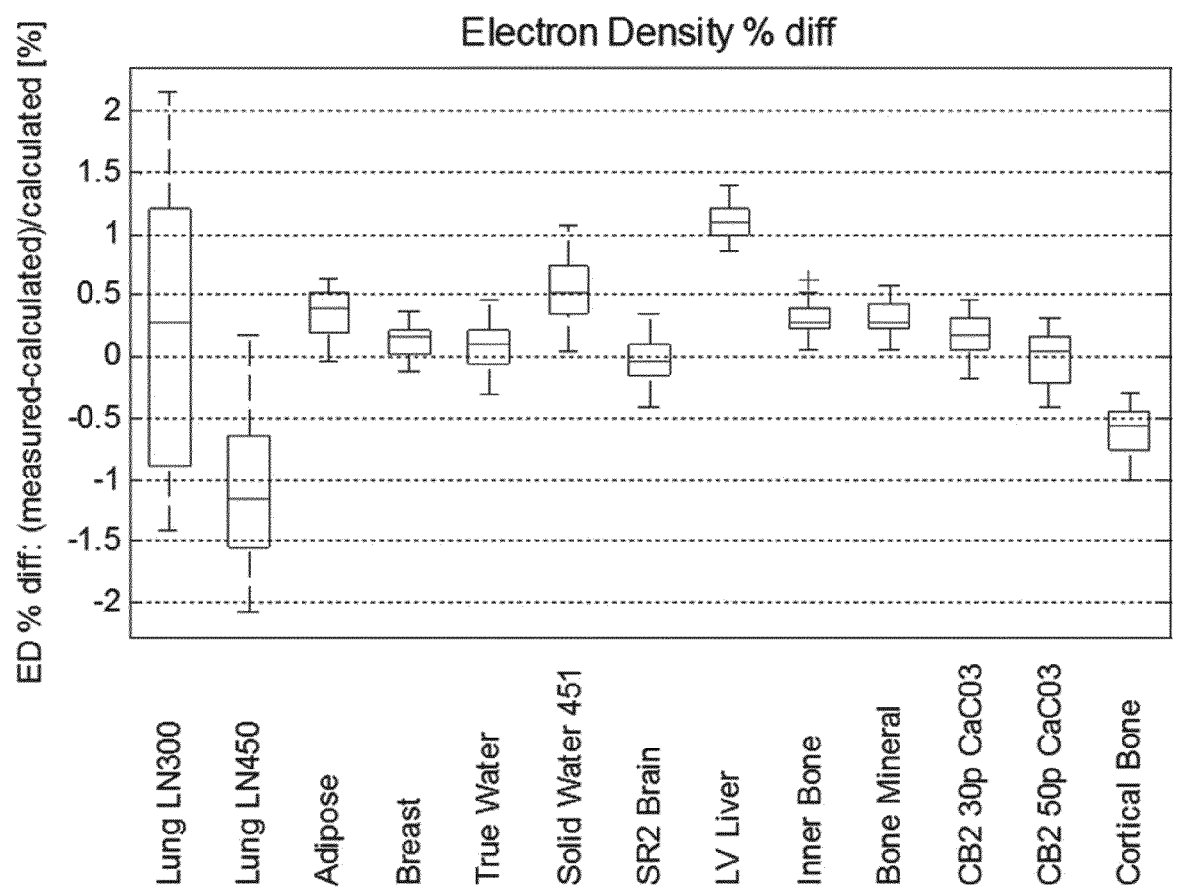
Figure 5:
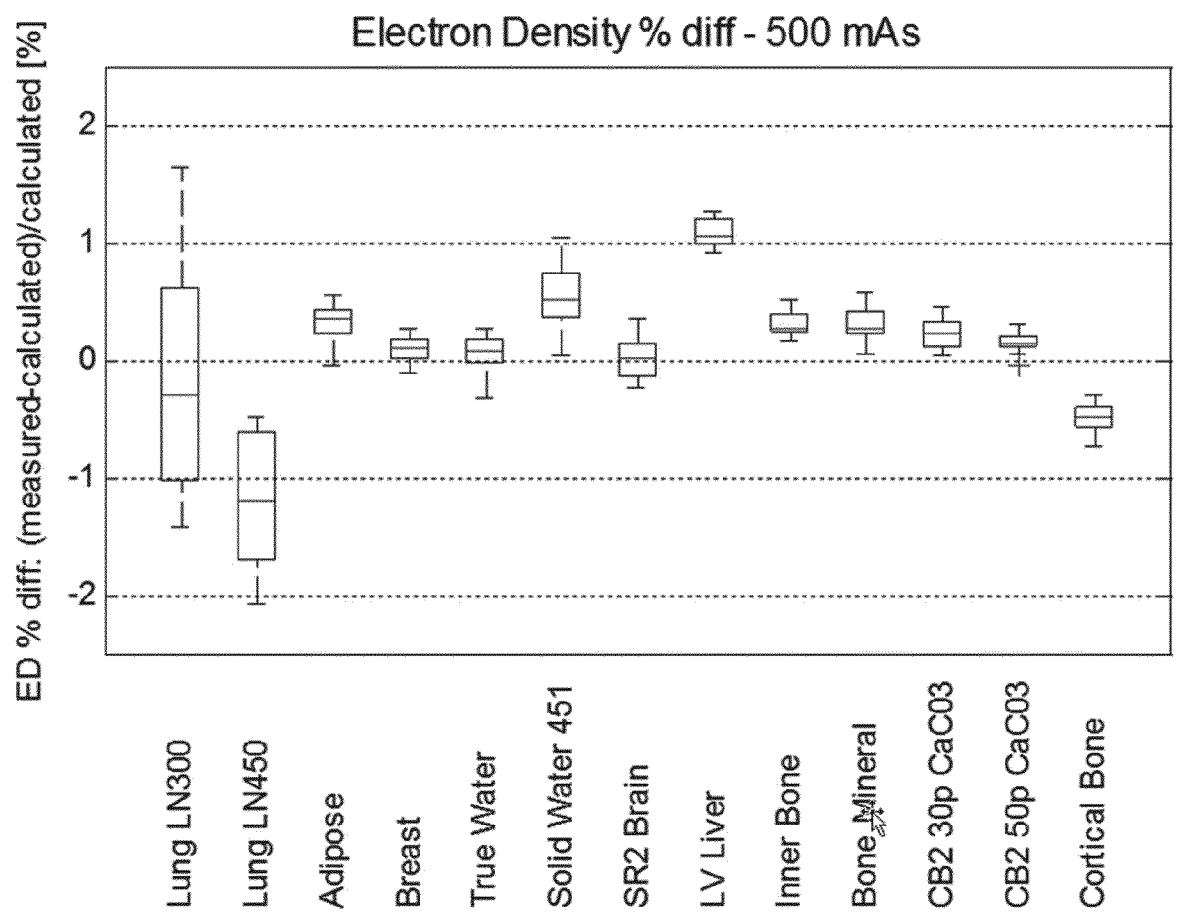
Figure 6:
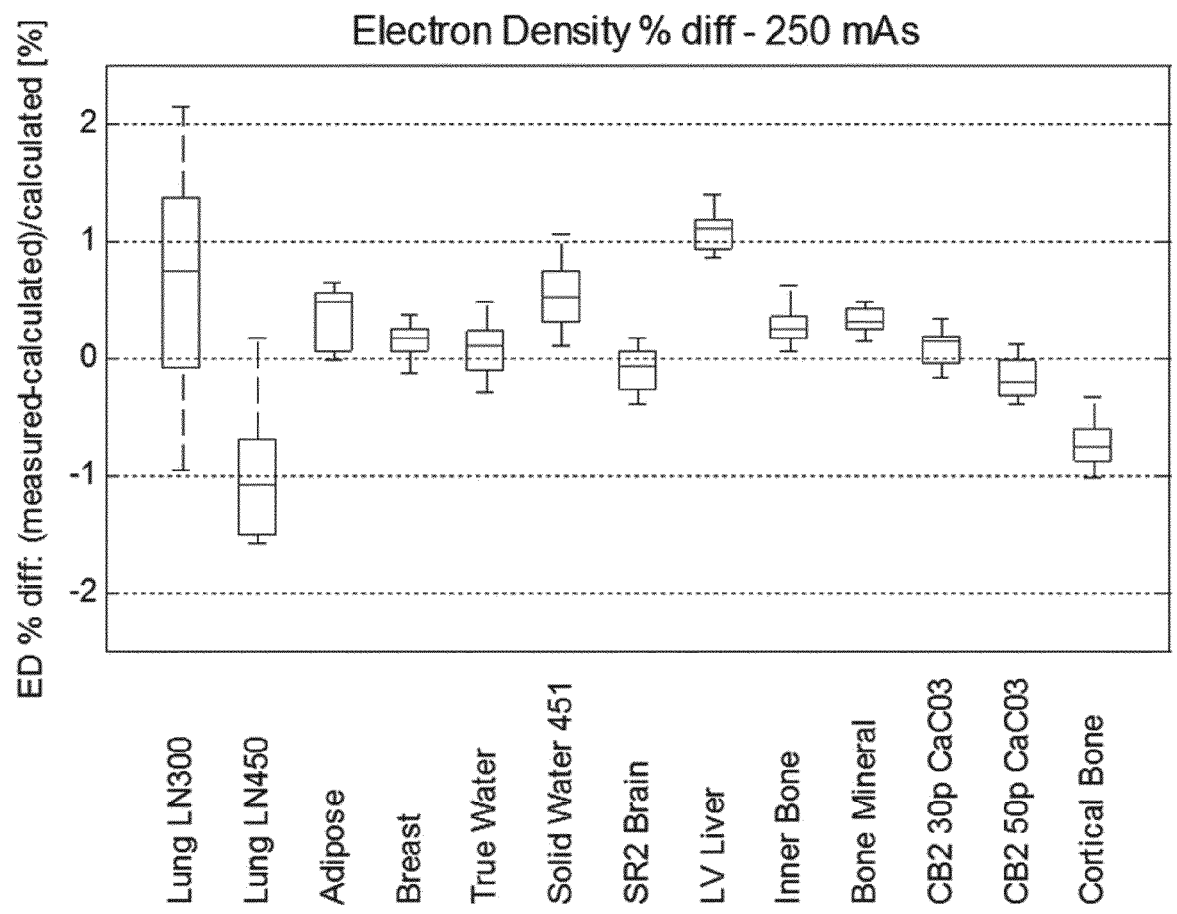

It is an advantage of such particular embodiments to choose the L1 norm over the common L2 norm corresponding to the residual sum of squared errors (minimizing the sum of the square of the differences between the target value (obtained value) and the predicted value) because the L1 norm does not attribute additional weight to possible outliers. It is furthermore of particular advantage to reduce the residual sum of errors in absolute electron density differences below a given error tolerance bound instead of using for example the more common approach of reducing the residual sum of errors in relative electron density differences (ratios) that would result in more uniformly distributed errors over the range of investigated electron density values. The reason therefore may be the aim to divert additional weight to tissues having high expected electron densities, e.g. bony tissues, since the accuracy of these tissues is of higher importance for radiation planning FIG. 2 show that the fitting procedure of a first order polynomial predicting electron densities achieves a good agreement between reported electron density values of tissue substitutes (circles) as given by the ICRU 44 report and predicted electron density values for those tissue substitutes (solid line), even for tissue substitutes having high electron densities (measured in Fig. xx in units of electron density in water).

Whereas in some embodiments the conversion method uses decomposition coefficients that are provided in form of a CT dataset that may be obtained from measured CT attenuation coefficients by solving a system of linear equations as indicated in Eq. 1 for a given energy pair and base material pair, the preparation method requires means to provide decomposition coefficients as inputs to the generalized prediction model, e.g. model in Eq. 3, for a set of given material mixtures, e.g. all the tissue substitutes of the ICRU 44 report. In particular embodiments of the invention this is solved by establishing a system of linear equations for a given energy pair ($E_1, E_2$) and base material pair, similar to Eq. 1, but replacing the attenuation coefficient measured by a CT scan, $\mu_{x,CT}$, by obtained reference values of the attenuation coefficients specific to a reported tissue substitute, $\mu_{i,report}$, at said energies $E_1$, $E_2$. This system of linear equations is then solved for the decomposition coefficients $c_1$, $c_2$. However, other functional relationships between decomposition coefficients and obtained reference attenuation coefficients may be implemented, for instance nonlinear fitted parameter models. It is an advantage of particular embodiments of the invention that the selected base material pair $b_1$, $b_2$ used to provide decomposition coefficients as inputs to the generalized prediction model, e.g. model in Eq. 3, may be the same base material pair that is used by the conversion method upon electron density prediction based on recorded CT datasets. This is useful because no further calibration steps with regard to other base material choices is required. Embodiments of the invention may use water and a $CaCl_2$ solution as base material pair. In addition, it proves advantageous to use base materials characterized and calibrated, e.g. by tissue characterization phantoms, for their use in dual-energy CT as they include relevant measurement aspects that influence the values of the decomposition coefficients and therefore have an impact on the predicted electron density values of actual CT datasets. Such effects may comprise the polychromatic spectrum of the X-ray beam and the energy spectral response of the detector. In alternative embodiments of the invention, pure, theoretical base material pairs may be used whose attenuation coefficients may be obtained from reported data. This may be an advantage in numerical studies that do not have to be strictly matched to experimental CT conditions. In particular embodiments of the present invention the attenuation coefficients specific to a reported tissue substitute, $\mu_{i,report}$, at the at least two energies $E_1$, $E_2$ are inferred from tabulated mass attenuation coefficients $\mu_{m,j}$ of tissue components listed in the NIST XCOM data and from the respective mass fractions $\omega_j$ of tissue components listed in the ICRU 44 report, owing to the relation indicated in Eq. 5.

$$\mu_{i,report}(E_k)/\rho_{avg} = \sum_j^{Nr \cdot coeff\ tissue\ i} \omega_j \mu_{m,j} \qquad \text{(Eq. 5)}$$

A good prediction accuracy of electron densities has been verified experimentally for an embodiment of the present invention. For such an embodiment a linear electron density prediction model, e.g. a model of the type indicated in Eq. 3, has been used, having three free parameters that are fit according to embodiments of the preparation method that have been described hereinabove. In the experiment, the fitted linear model has been used as input to the conversion method that turned data from six dual-energy CT scans performed on a Gammex 467 Tissue Characterization Phantom at two different dose levels—3 scans at 250 mAs (CTDIvol=28.9 mGy) and 3 scans at 500 mAs (CTDIvol=57.8 mGy)—into electron density estimates for a total of thirteen tissue substitutes comprising among others cortical bone, breast, adipose, and lung LN300. FIG. 3 to FIG. 6 relate to the absolute and relative difference between measured and predicted electron densities relative to the electron density of water. Absolute differences in electron densities are typically in the range of ±1.5% relative to the electron density of water with most tissue types having first and third quartiles in the ±0.5% range including high electron density tissue substitutes such as inner bone, bone mineral, and $CaCO_3$. Relative differences in the median electron densities are typically below ±0.5% relative to the electron density of water, the only exceptions being liver and lung. It is also seen from a comparison between FIG. 5 and FIG. 6 that a higher dose scan at 500 mAs reduces the error margins as obtained from multiple scan repetitions for most tissue substitutes when compared to a lower dose of 250 mAs only.

In embodiments of the invention, the fitted parameters obtained by carrying out the steps of the preparation method may be stored on a storage medium, such as a computer-readable medium comprising CD-ROMs, DVDs, floppy disks, USB devices, SD cards, hard drives, flash drives, DRAM, etc. These parameters may be duplicated and distributed for use in CT scanning systems that seek to convert multi-energy CT datasets into electron density datasets. In some embodiments the CT scanning system may comprise a data processing device, e.g. a computer, computer cluster, GPU array, microprocessor or FPGA, that first reads the stored fitted parameters from the computer-readable medium and uses them as inputs for the conversion method which may also be carried out by said processing device. In other embodiments of the invention, the fitted parameters may be part of a computer program that performs the steps of the conversion method when executed on a processing device. In such embodiments the fitted parameters of the generalized model are part of the installed computer program and may be retrieved by it at any time. The computer program will typically receive online or offline data acquired by a CT scanning hardware on which it operates the conversion method in order to obtain electron density datasets that may be visualized or displayed as electron density images. These images may be used as input to subsequent radiotherapy planning systems or ion stopping power calculations. In other embodiments of the invention a processing device may receive the stored fitted parameter values of the preparation method, the CT dataset, or both, as a transmission signal over a network link and thereafter convert the CT dataset to electron density datasets executing the instructions of the conversion method that may be installed on said computer or may be received via said network link too.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The invention claimed is:

1. A computer-implemented method for converting spectral CT datasets into electron density datasets, the method comprising:

retrieving at least a set of fitted parameter of a function predicting electron densities of material mixtures;

modeling first attenuation coefficients representing attenuation characteristics of at least one material mixture as a combination of second attenuation coefficients of constituent elements of the at least one material mixture for a first set of at least two different values of physical phenomena contributing to attenuation;

determining base components of a material decomposition model for each of the at least one material mixtures, each component being a function of the first attenuation coefficients, the determining being performed by solving a system of equations relating said first attenuation coefficients to combinations of known base material attenuation coefficients determined by a second set of at least two different values of physical phenomena contributing to attenuation;

fitting a parametrized function of said two base components to an obtained reference value for the electron densities of said material mixtures, thus obtaining a function with a set of fitted parameters predicting electron densities of the material mixtures; and obtaining a spectral CT dataset comprising a plurality of measurement points, extracting base components for each measurement point within the CT dataset, and applying the function with the set of fitted parameters to the extracted base components, thus obtaining an electron density dataset, wherein said fitting a parametrized function of said two base components to obtained electron densities of said material mixtures involves fitting a polynomial function with order higher than one of said two base components to obtained electron densities of said material mixtures, wherein the obtained electron density data set is displayed as one or more electron density images that provide accurate calculations of proton stopping powers, thereby enabling to lower administering of radiation doses and to better target irradiation spots leaving surrounding tissue intact.

2. The method according to claim 1, wherein said combination of second attenuation coefficients of constituent elements of the at least one material mixture is a linear superposition.

3. The method according to claim 2, wherein said second attenuation coefficients of constituent elements of the at least one material mixture is expressed as weighted mass attenuation coefficients, the weight corresponding to the given mass fraction of a constituent element in the material mixture.

4. The method according to claim 1, wherein said second attenuation coefficients of constituent elements of the at least one material mixture is inferred from obtained data on tissue composition and obtained data on mass attenuation coefficients.

5. The method according to claim 1, wherein said system of equations relating said first attenuation coefficients to combinations of known base material attenuation coefficients at the at least two different values of physical phenomena contributing to attenuation is a system of linear equations.

6. The method according to claim 1, wherein said fitting a parametrized function of said two base components to obtained electron densities of said material mixtures is achieved by adapting the function parameters in a way such that the sum of residual errors between said predicted electron densities of said material mixtures and said obtained electron densities of said material mixtures is below a threshold value according to an error measure.

7. The method according to claim 6, wherein said error measure for said sum of residual errors between said predicted electron densities of said material mixtures and said obtained electron densities of said material mixtures is the L1 error norm.

8. A data processing device for converting spectral CT datasets into electron density datasets, the device comprising:

a first input port configured to receive at least a set of fitted parameter of a function predicting electron densities of material mixtures;

a second input port configured to receive a spectral CT dataset comprising a plurality of measurement points; and at least one processor circuitry configured to:

model first attenuation coefficients representing attenuation characteristics of at least one material mixture as a combination of second attenuation coefficients of constituent elements of the at least one material mixture for a first set of at least two different values of physical phenomena contributing to attenuation, determine base components of a material decomposition model for each of the at least one material mixtures, each component being a function of the first attenuation coefficients, the determining being performed by solving a system of equations relating said first attenuation coefficients to combinations of known base material attenuation coefficients determined by a second set of at least two different values of physical phenomena contributing to attenuation, fit a parametrized function of said two base components to an obtained reference value for the electron densities of said material mixtures, thus obtaining a function with a set of fitted parameters predicting electron densities of the material mixtures; and obtain a spectral CT dataset comprising a plurality of measurement points, extract base components for each measurement point within the CT dataset, and apply the received function with the set of fitted parameters to the extracted base components, such that an electron density dataset is obtained, wherein the fitting a parametrized function of said two base components to obtained electron densities of said material mixtures involves fitting a polynomial function with order higher than one of said two base components to obtained electron densities of said material mixtures, and wherein the obtained electron density data set is displayed as one or more electron density images that provide accurate calculations of proton stopping powers, thereby enabling to lower administering of radiation doses and to better target irradiation spots leaving surrounding tissue intact.

9. A non-transitory computer-readable data carrier comprising one or more executable instructions stored thereon which, when executed by at least one processor circuity, cause the at least one processor circuitry to perform a method comprising:

retrieving at least a set of fitted parameter of a function predicting electron densities of material mixtures;

modeling first attenuation coefficients representing attenuation characteristics of at least one material mixture as a combination of second attenuation coefficients of constituent elements of the at least one material mixture for a first set of at least two different values of physical phenomena contributing to attenuation;

determining base components of a material decomposition model for each of the at least one material mixtures, each component being a function of the first attenuation coefficients, the determining being performed by solving a system of equations relating said first attenuation coefficients to combinations of known base material attenuation coefficients determined by a second set of at least two different values of physical phenomena contributing to attenuation;

fitting a parametrized function of said two base components to an obtained reference value for the electron densities of said material mixtures, thus obtaining a function with a set of fitted parameters predicting electron densities of the material mixtures; and obtaining a spectral CT dataset comprising a plurality of measurement points, extracting base components for each measurement point within the CT dataset, and applying the function with the set of fitted parameters to the extracted base components, thus obtaining an electron density dataset, wherein said fitting a parametrized function of said two base components to obtained electron densities of said material mixtures involves fitting a polynomial function with order higher than one of said two base components obtained electron densities of said material mixtures, wherein the obtained electron density data set is displayed as one or more electron density images that provide accurate calculations of proton stopping powers, thereby enabling to lower administering of radiation doses and to better target irradiation spots leaving surrounding tissue intact.

* * * * *